United States Patent [19]

Haikala et al.

[11] Patent Number: 5,512,572
[45] Date of Patent: Apr. 30, 1996

[54] ANTI-ISCHEMIC MEDICAMENT

[75] Inventors: Heimo O. Haikala, Espoo; Juoko M. Levijoki, Helsinki; Reijo J. Bäckström, Helsinki; Pentti T. Nore, Helsinki; Erkki J. Honkanen, Espoo, all of Finland

[73] Assignee: Orion-yhtyma Oy, Espoo, Finland

[21] Appl. No.: 331,607

[22] PCT Filed: May 5, 1993

[86] PCT No.: PCT/FI93/00191
§ 371 Date: Nov. 22, 1994
§ 102(e) Date: Nov. 22, 1994

[87] PCT Pub. No.: WO93/21921
PCT Pub. Date: Nov. 11, 1993

[30] Foreign Application Priority Data

May 6, 1992 [GB] United Kingdom ............ 9209769

[51] Int. Cl.⁶ ..................................... A61K 31/50
[52] U.S. Cl. ..................................... 514/247
[58] Field of Search ............................ 514/247

[56] References Cited

U.S. PATENT DOCUMENTS

| | | | |
|---|---|---|---|
| 4,766,123 | 8/1988 | Coates | 514/247 |
| 4,962,110 | 10/1990 | Emmett et al. | 514/252 |
| 5,109,575 | 5/1991 | Haikala et al. | 514/247 |
| 5,122,524 | 6/1992 | Haikala et al. | 514/242 |

FOREIGN PATENT DOCUMENTS

| | | |
|---|---|---|
| 0233745 | 8/1987 | European Pat. Off. . |
| 0310313 | 4/1989 | European Pat. Off. . |
| 0311322 | 4/1989 | European Pat. Off. . |
| 0383449 | 8/1990 | European Pat. Off. . |
| WO92/12135 | 7/1992 | WIPO . |

*Primary Examiner*—Kimberly Jordan
*Attorney, Agent, or Firm*—Burns, Doane, Swecker & Mathis

[57] ABSTRACT

A method for preventing or treating myocardial ischemia in a mammalian organism is disclosed. The compound [[4-(1,4,5,6-tetrahydro-4-methyl-6-oxo-3-pyridazinyl)phenyl]hydrazono]propanedinitrile or its enantiomer or a pharmaceutically acceptable salt there is administered to a mammalian organism in need of such prevention or treatment. The compound may be administered in its racemic form or in a form which is substantially free of the (+)-enantiomer or substantially free of the (−)-enantiomer.

6 Claims, 1 Drawing Sheet

ANTI-ISCHEMIC MEDICAMENT

This application is a 371 of PCT/FI93/00191, filed May 5, 1993.

The present invention relates to the use of [[4-(1,4,5,6-tetrahydro-4-methyl-6-oxo-3-pyridazinyl)phenyl]hydrazono]propanedinitrile (I) or its enantiomers or pharmaceutically acceptable salts thereof in the manufacture of a medicament for the treatment or prevention of myocardial ischemia.

[[4-(1,4,5,6-tetrahydro-4-methyl-6-oxo-3-pyridazinyl)phenyl]hydrazono]propanedinitrile (I) has been earlier described in European patent application EP 383449. It has been shown that compound (I) may be potent in the treatment of congestive heart failure. The optically pure enantiomers of this compound has previously been described in the patent application PCT/FI92/00003. It has now been revealed that compound (I) and its optically active enantiomers also have significant anti-ischemic properties.

The method for the preparation of compound (I) and the resolution of its optically active (−) and (+) enantiomers are described in the patent applications mentioned above. Salts of these compounds may be prepared by known methods. Pharmaceutically acceptable salts are useful as active medicaments, however, preferred salts are the salts with alkali or alkaline earth metals.

In EP 383449 it was shown that compound (I) has significant calcium dependent binding to troponin and is a potent inhibitor of PDE III enzyme. Like other PDE III inhibitors, such as pimobendan and milrinone, compound (I) increases contractility of the cardiac muscle and produces vasodilatation and has therefore utility in the treatment of congestive heart failure. The anti-ischemic utility of positive inotropic compound (I) which is a potent PDE III inhibitor was unexpected because arrhythmic effects have often been observed in connection with PDE III inhibitors. We have found that, unlike pimobendan or milrinone, compound (I) can decrease calcium influx. This may play some role in the observed new effect of compound (I) and its enantiomers.

Figure 1:
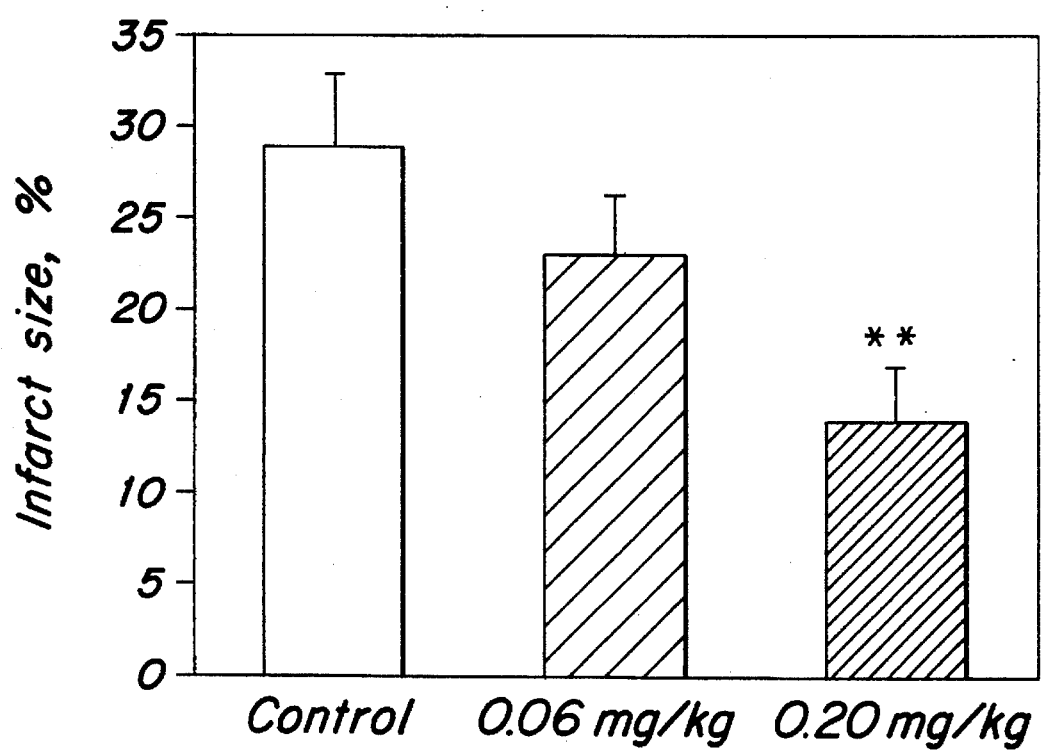
FIG 1 shows the dose dependent effect of compound (I) on infarct size.

The anti-ischemic compound according to the invention is formulated into dosage forms using the principles known in the art. It is given to mammalian organisms, i.e., humans, a patient as such or in combination with suitable pharmaceutical excipients in the form of tablets, dragees, capsules, suppositories, emulsions, suspensions or solutions whereby the contents of the active compound is in the formulation from about 0.5 to 100% per weight. In general, the compound of the invention may be administered to man in oral doses ranging from about 1 to 100 mg per day once a day or divided into several doses. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions of the present invention have anti-ischemic activity and are of use in the treatment and prevention of myocardial ischemia. Such conditions can be treated by administration of the compounds according to the invention for example orally, rectally or parenterally.

The anti-ischemic properties of the compounds according to the invention are demonstrated below.

The effects of [[4-(1,4,5,6-tetrahydro-4-methyl-6-oxo-3-pyridazinyl)phenyl]hydrazono]propanedinitrile on ventricular arrhytmias, survival rate and infarct size after coronary artery ligation were studied in conscious rats (male Sprague-Dawley rats). Anesthetized rats were opened at the fourth intercostal space and a silk loop was placed around the left main coronary artery, about 3 mm from its origin. After complete recovery (7–10 days) from this preliminary surgery, the coronary ligature was tightened in the conscious rats to produce acute coronary artery occlusion. [[4-(1,4,5,6-tetrahydro-4-methyl-6-oxo-3-pyridazinyl)phenyl] hydrazono]propanedinitrile in doses of 0.06 and 0.20 mg/kg (in NaCl solution) was given intravenously 5 min prior to the ligation. A bipolar ECG was recorded continuously. The survival rate and the incidence of arrhytmias were registered in accordance with the Lambeth Conventions. In the animals that survived for 16 hours, the size of the infarcted area was measured after staining with nitroblue-tetrazolium dye.

The results (Table 1) show that [[4-(1,4,5,6-tetrahydro-4-methyl-6-oxo-3-pyridazinyl)phenyl] hydrazono]propanedinitrile increased the survival rate and decreased the incidence of arrhytmias as compared with the control group. In addition the incidence of ventricular tachycardia decreased from 82% in the controls to 53% after the lower and to 28% ($p<0.01$) after the higher dose (this data not shown in Table 1). FIG. 1 shows that [[4-(1,4,5,6-tetrahydro-4-methyl-6-oxo-3-pyridazinyl) phenyl]hydrazono]propanedinitrile also decreased the infarct size dose-dependently.

TABLE 1

| Dose (mg/kg) | n | Acute phase Survival (%) | No arrhythmia (%) |
|---|---|---|---|
| Control | 17 | 65 | 18 |
| 0.06 | 15 | 93* | 33 |
| 0.20 | 14 | 100** | 64** |

*$p < 0.05$
**$p < 0.01$

The effects of optically pure enantiomers of [[4-(1,4,5,6-tetrahydro-4-methyl-6-oxo-3-pyridazinyl) phenyl]hydrazono]propanedinitrile were also studied. The experiment was performed as above with the exception that the ligation was placed around the left coronary artery about 2 mm from its origin. The doses were 0.06 and 0.20 mg/kg (in $Na_2HPO_4$ solution) for both (−) and (+) enantiomer of [[4-(1,4,5,6-tetrahydro-4-methyl-6-oxo-3-pyridazinyl)phenyl]-hydrazono] propanedinitrile. The results for the (−)-enantiomer are shown in Table 2 and for the (+)-enantiomer in Table 3. Both enantiomers increased the number of animals which did not develop any arrhythmias. In addition, the (+)-enantiomer showed survival rate increasing effect.

TABLE 2

| Dose (mg/kg) | n | Acute phase Survival (%) | No arrhythmia (%) |
|---|---|---|---|
| Control | 17 | 76 | 0 |
| 0.06 | 11 | 64 | 18* |
| 0.20 | 17 | 65 | 35** |

*$p < 0.05$
**$p < 0.01$

TABLE 3

| Dose (mg/kg) | n | Acute phase | |
|---|---|---|---|
| | | Survival (%) | No arrhythmia (%) |
| Control | 20 | 40 | 5 |
| 0.06 | 14 | 57 | 21 |
| 0.20 | 13 | 69* | 15 |

*$p < 0.05$
**$p < 0.01$

The results indicate that [[4-(1,4,5,6-tetrahydro-4-methyl-6-oxo-3-pyridazinyl)phenyl]hydrazono] propanedinitrile and its enantiomers afford significant protection against ischemia-induced arrhythmias and the development of irreversible myocardial damage. These compounds have therefore utility as anti-ischemic agents in the treatment or prevention of myocardial ischemia.

We claim:

1. A method for treating myocardial ischemia in a mammalian organism in need of such treatment, said method comprising administering an effective amount to treat myocardial ischemia of [[4-(1,4,5,6-tetrahydro-4-methyl-6-oxo-3-pyridazinyl)phenyl]-hydrazono] propanedinitrile or its enantiomer or a pharmaceutically acceptable salt thereof.

2. A method according to claim 1, wherein [[4-(1,4,5,6-tetrahydro-4-methyl-6-oxo-3-pyridazinyl)phenyl] hydrazono]propanedinitrile is substantially free of the (+)-enantiomer.

3. A method according to claim 1, wherein [[4-(1,4,5,6-tetrahydro-4-methyl-6-oxo-3-pyridazinyl)phenyl] hydrazono]propanedinitrile is substantially free of the (−)-enantiomer.

4. A method for preventing myocardial ischemia in a mammalian organism, said method comprising administering to a mammalian organism in need of such prevention an effective amount to prevent myocardial ischemia of [[4-(1,4,5,6-tetrahydro-4-methyl-6-oxo-3-pyridazinyl) phenyl]hydrazono]propanedinitrile or its enantiomer or a pharmaceutically acceptable salt thereof.

5. A method according to claim 4, wherein [[4-(1,4,5,6-tetrahydro-4-methyl-6-oxo-3-pyridazinyl) phenyl]hydrazono]propanedinitrile is substantially free of the (+)-enantiomer.

6. A method according to claim 4, wherein [[4-(1,4,5,6-tetrahydro-4-methyl-6-oxo-3-pyridazinyl)phenyl] hydrazono]propanedinitrile is substantially free of the (−)-enantiomer.

* * * * *